US012779162B2

(12) United States Patent
Dong et al.

(10) Patent No.: US 12,779,162 B2
(45) Date of Patent: Nov. 3, 2026

(54) DEVICE AND METHOD FOR WEANING VENTILATOR PATIENTS BASED ON MIXED GASES

(71) Applicant: GUANGZHOU LANSWICK MEDICAL TECHNOLOGY CO., LTD., Guangzhou (CN)

(72) Inventors: Hui Dong, Guangzhou (CN); Longchao Zhao, Guangzhou (CN); Caixin Sun, Guangzhou (CN)

( * ) Notice: Subject to any disclaimer, the term of this patent is extended or adjusted under 35 U.S.C. 154(b) by 656 days.

(21) Appl. No.: 18/271,668

(22) PCT Filed: Mar. 10, 2023

(86) PCT No.: PCT/CN2023/080731
§ 371 (c)(1),
(2) Date: Jul. 11, 2023

(87) PCT Pub. No.: WO2023/213138
PCT Pub. Date: Nov. 9, 2023

(65) Prior Publication Data

US 2025/0010013 A1 Jan. 9, 2025

(30) Foreign Application Priority Data

May 5, 2022 (CN) ......................... 202210480182.1

(51) Int. Cl.
*A61M 16/10* (2006.01)
*A61M 16/00* (2006.01)
*A61M 16/12* (2006.01)

(52) U.S. Cl.
CPC .... *A61M 16/1005* (2014.02); *A61M 16/0066* (2013.01); *A61M 16/024* (2017.08);
(Continued)

(58) Field of Classification Search
CPC .. A61M 16/12; A61M 16/024; A61M 16/022; A61M 16/026; A61M 2202/0225;
(Continued)

(56) References Cited

U.S. PATENT DOCUMENTS 5,320,093 A * 6/1994 Raemer ............... A61M 16/085 128/914
2002/0174866 A1* 11/2002 Orr ........................ A61B 5/029 128/204.22
(Continued)

FOREIGN PATENT DOCUMENTS

EP 3115074 A1 * 1/2017 .......... A61M 16/024

OTHER PUBLICATIONS

Machine translation of EP 3115074 A1 (Year: 2017).*
Mechanical Ventilation, University of San Francisco (Year: 2013).*

*Primary Examiner* — Brandy S Lee
*Assistant Examiner* — Sara K Toich

(57) ABSTRACT

A method and device for solving ventilator weaning of patients based on mixed gas and device thereof, includes: mixing carbon dioxide and oxygen based on the initial mixed concentration, and delivering the mixed gas to the patient based on the ventilator device; real-time monitoring patient's partial pressure of carbon dioxide based on the delivery result, and based on the partial pressure of carbon dioxide, gradiently changing the initial mixed concentration of carbon dioxide and oxygen; obtaining the patient's respiratory muscle function data based on the gradient change result, and evaluating the respiratory muscle function data. By mixing a certain concentration of carbon dioxide gas and oxygen, the patient's respiratory nerve center can be stimulated, so as to ensure the patient's active breathing.

1 Claim, 5 Drawing Sheets

(52) U.S. Cl.
CPC ..... *A61M 16/12* (2013.01); *A61M 2202/0007* (2013.01); *A61M 2202/0208* (2013.01); *A61M 2202/0225* (2013.01); *A61M 2205/3303* (2013.01); *A61M 2205/3324* (2013.01); *A61M 2205/3331* (2013.01); *A61M 2205/50* (2013.01); *A61M 2230/005* (2013.01); *A61M 2230/202* (2013.01); *A61M 2230/208* (2013.01); *A61M 2230/432* (2013.01)

(58) Field of Classification Search
CPC ...... A61M 2230/202; A61M 2230/208; A61M 2205/3324; A61B 5/7246
See application file for complete search history.

(56) References Cited

U.S. PATENT DOCUMENTS

| | | | | |
|---|---|---|---|---|
| 2014/0288440 | A1* | 9/2014 | Asher | A61B 5/7267 600/484 |
| 2021/0016035 | A1* | 1/2021 | Euliano, II | A61B 5/0037 |
| 2025/0128004 | A1* | 4/2025 | Phillips | A61B 8/06 |

* cited by examiner

DEVICE AND METHOD FOR WEANING VENTILATOR PATIENTS BASED ON MIXED GASES

BACKGROUND OF THE PRESENT INVENTION

Field of Invention

The present invention relates to the field of ventilator technology, and more particular to a method and device for solving patient ventilator off-line problems on patients based on mixed gases.

Description of Related Arts

At present, when patients use a ventilator (usually oxygen O2 and air or mixed gas) to support their own breathing for a long time, their respiratory system function will degrade, they will lose their ability to breathe spontaneously, and "addiction" will appear. When the patient needs to be taken off-line, it is necessary to gradually restore the patient's own respiratory function with the help of certain functions of the ventilator. The recovery period is long, and the curative effect is unstable. Even off-line, there are often repetitions, that is, to use the ventilator again to support self-breathing. Increased patient distress during recovery of breathing;

Therefore, the present invention provides a method and device for solving the off-line of the patient's ventilator based on mixed gas. By mixing a certain concentration of carbon dioxide gas and oxygen, the patient's respiratory nerve center can be stimulated, thereby ensuring that the patient is stimulated to carry out active breathing, improve the stability of the treatment, ensure the effect and efficiency of the patient's respiratory function recovery, and reduce the pain of the patient when off-line.

SUMMARY OF THE PRESENT INVENTION

The invention provides a method and device for solving the off-line of a patient's ventilator based on mixed gas, which is used to stimulate the patient's respiratory nerve center by mixing a certain concentration of carbon dioxide gas with oxygen, thereby ensuring that the patient is stimulated to carry out active breathing. It improves the stability of the treatment, ensures the effect and efficiency of the patient's respiratory function recovery, and reduces the pain of the patient when offline.

The invention provides a method for solving the off-line of the patient's ventilator based on the mixed gas, comprising:

Step (1): Mix carbon dioxide and oxygen based on the initial mixing concentration and deliver the mixture to the patient based on the ventilator device;

Step (2): Monitor the patient's partial pressure of carbon dioxide in real time based on the delivery result, and change the initial mixed concentration of carbon dioxide and oxygen in a gradient based on the partial pressure of carbon dioxide;

Step (3): Obtain the patient's respiratory muscle function data based on the gradient change result, and evaluate the respiratory muscle function data, and complete the off-line of the patient's ventilator based on the evaluation result.

Preferably, a method for solving the off-line of a patient's ventilator based on mixed gas, in step (1), mixing carbon dioxide and oxygen based on the initial mixed concentration, comprising:

obtaining current working parameters of the ventilator device, and determining the target oxygen supply mode of the ventilator device based on the current working parameters, wherein the target oxygen supply mode is a standard oxygen supply mode or an offline oxygen supply mode;

when the target oxygen supply mode is a standard oxygen supply mode, switching the target oxygen supply mode of the ventilator device based on a preset switching valve;

when the target oxygen supply mode is an offline oxygen supply mode, obtaining the control range of the breathing apparatus for the carbon dioxide concentration, and determining the initial mixed concentration of carbon dioxide based on the control range; and based on the initial mixing concentration, the carbon dioxide and oxygen are respectively input into the target container through the airway tube for mixing to obtain a mixed gas of carbon dioxide and oxygen.

Preferably, a method for solving the off-line of the patient's ventilator based on the mixed gas, based on the initial mixed concentration, respectively mixing the carbon dioxide and oxygen into the target container through the airway tube, comprising:

sampling the carbon dioxide based on a preset sampling device, and detecting the concentration of the sampled carbon dioxide to obtain the detection concentration of the carbon dioxide;

comparing the detected concentration with the initial mixed concentration;

wherein if there is a difference between the detected concentration and the initial mixed concentration, it is determined that there is a defect in the mixing of carbon dioxide and oxygen, and an alarm operation is performed, and the operation of inputting the mixed gas to the patient is terminated simultaneously;

otherwise, it is determined that the mixing of carbon dioxide and oxygen is qualified, and the process of mixing carbon dioxide and oxygen is detected in real time until the patient is off the ventilator.

Preferably, a method for solving a patient ventilator off-line based on a mixed gas, in step (1), delivering the mixed gas to the patient based on the ventilator device, comprising:

acquiring the patient's sign parameters, and determine the oxygen supply pressure and oxygen supply rate to the patient based on the sign parameters;

adjusting the operating parameters of the ventilator device based on the oxygen supply pressure and oxygen supply rate, and detecting the airtightness of the inspiratory tube of the ventilator device based on the adjustment result;

delivering a mixture of carbon dioxide and oxygen to the patient based on the inspiratory tube if the airtight seal is intact; and otherwise, replacing the inspiratory tube, and delivering the mixed gas to the patient based on the result of the replacement.

Preferably, a method for solving the off-line of a patient ventilator based on a mixed gas, based on the inspiratory tube The mixed gas of carbon dioxide and oxygen is delivered to the patient, comprising:

obtaining the time information of the patient receiving the mixed gas of carbon dioxide and oxygen and the gas volume of the mixed gas, and obtain the identity information of the patient; and constructing the patient treatment electronic data sheet based on the time information, gas volume and identity information, and typesetting the patient treatment electronic data table to obtain the target recording areas of the time information, gas volume and identity information respectively;

The time information, gas volume and identity information are recorded based on the target recording area, and the gas volume of the mixed gas received by the patient in the patient treatment electronic data sheet is updated synchronously.

Preferably, a method for solving the off-line of the patient's ventilator based on the mixed gas, in step (2), the partial pressure of carbon dioxide of the patient is monitored in real time based on the delivery result, and the initial mixed concentration of carbon dioxide and oxygen is gradually changed based on the partial pressure of carbon dioxide, comprising:

Based on the ventilator device, the mixed gas of the initial mixed concentration is continuously input to the patient for a preset period of time, and the partial pressure of carbon dioxide of the patient is monitored in real time, wherein the partial pressure of carbon dioxide comprises arterial partial pressure of carbon dioxide and end-tidal partial pressure of carbon dioxide;

determining the target value of the partial pressure of carbon dioxide of the patient at different time points based on the monitoring results, and obtaining a numerical sequence of the partial pressure of carbon dioxide of the patient within a preset time period;

matching the target chart from the preset chart template library based on the numerical sequence, and determining the horizontal and vertical coordinate legends of the two-dimensional coordinates of the target chart based on the attribute information of the preset time period and the target value of the numerical sequence, Among them, the legend on the abscissa is time, and the legend on the ordinate is the target value of the numerical sequence;

determining the configuration parameters of the target chart, and performing format conversion on the numerical sequence of the partial pressure of carbon dioxide based on the configuration parameters to obtain the partial pressure of carbon dioxide visual graph;

determining the maximum value and the minimum value of the partial pressure of carbon dioxide of the patient in the preset time period based on the partial pressure of carbon dioxide visual map, and determine the carbon dioxide concentration of the patient based on the maximum value and the minimum value of carbon dioxide Pressure fluctuation range;

comparing the stated fluctuation range with the standard allowable range;

wherein if the fluctuation range is not within the allowable range of the standard, it is determined that the patient's inhalation of the mixed gas is abnormal;

otherwise, it is determined that there is no abnormality in the patient's inhalation of the mixed gas, and at the same time, the pH value in the patient's body is obtained;

determining the difference between the pH value and the standard pH value, and when the difference is within the preset allowable fluctuation range, it is determined that the patient has adapted to the mixed gas of the initial mixed concentration, and the ventilator Device feedback judgment result.

Based on the received feedback determination result, control the ventilator device to change the initial mixed concentration of carbon dioxide and oxygen by gradient, and continuously monitor the partial pressure of carbon dioxide of the patient until the initial mixed concentration reaches the gradient change The maximum allowed value, wherein the allowed range of the gradient change is 1%-6%.

Preferably, a method for solving the off-line of the patient ventilator based on the mixed gas, so as to judge that there are abnormalities in the inhalation of the gas mixture by the patients, comprising:

obtaining the comparison result between the fluctuation range and the standard allowable range, and when it is determined that the patient's inhalation of the mixed gas is abnormal, generate a target control instruction;

based on the target control instruction, controlling the ventilator device to stop delivering the mixed gas to the patient, and collecting a preset amount of the mixed gas, and at the same time acquiring the current sign data of the patient, wherein the sign data at least one;

detecting the mixed gas, respectively determining the ratio of carbon dioxide and oxygen in the mixed gas example, and verifying the ratio based on the preset ratio based on the ratio preset;

wherein if it fails to pass the verification, it is determined that the ventilator device has a defect in the mixing process of the carbon dioxide and oxygen, and a first alarm is carried out; and if the verification is passed, then the current sign data of the patient is analyzed to determine whether there is any abnormality in the current characteristic data of the patient, and if there is any abnormality, the second alarm is carried out;

recording first alarm and the second alarm respectively to obtain the abnormal situation report sheet of the patient in the off-line process of the ventilator.

Preferably, a method for solving the off-line of the patient's ventilator based on the mixed gas, in step (3), the patient's respiratory muscle function data is obtained based on the gradient change result, and the respiratory muscle function data is evaluated, and the patient's respiratory muscle function data is evaluated based on the evaluation result. Ventilator off-line, comprising:

obtaining the respiratory waveform data of the patient after gradiently changing the initial mixed concentration of the mixed gas based on the preset sensor, and fitting the respiratory waveform data to obtain the respiratory wave curve of the patient;

obtaining a reference respiratory wave curve, and superimposing the reference respiratory wave curve with the patient's respiratory wave curve, wherein the reference respiratory wave curve is obtained from training based on historical training data;

determining a difference area between the respiratory wave curve and the reference respiratory wave curve based on the superposition result domain, and extract the waveform features of the respiratory wave curve in the difference area;

determining curve parameters of the patient's respiratory wave curve in the difference area based on the waveform features, and treating the curve parameters to obtain the breathing data of the patient in the difference area;

extracting the attribute information of the respiratory data, and matching the target data cleaning rules from the preset data cleaning rule base based on the attribute information;

- cleaning the breathing data based on the target data cleaning rules to obtain the respiratory muscle function data of the patient;
- constructing a spontaneous breathing capacity assessment model, and inputting the respiratory muscle function data into the spontaneous breathing capacity assessment model for processing, determining the current respiratory rate of the patient, and simultaneously determining the respiratory intensity of the patient based on the current respiratory rate;
- Respectively determining the weight of the respiratory rate and respiratory intensity in the evaluation process of spontaneous breathing ability value, and obtaining the comprehensive evaluation value of the patient's current spontaneous breathing ability based on the weight value;
- displaying comprehensive evaluation value of the patient's current spontaneous breathing ability on the ventilator device, and at the same time, transmitting the comprehensive evaluation value of the patient's current spontaneous breathing ability to the doctor's smart terminal to complete the evaluation of the patient's spontaneous breathing ability.

Preferably, a method for solving the off-line of the patient's ventilator based on the mixed gas, wherein based on the weight value, obtaining the comprehensive evaluation value of the patient's current spontaneous breathing ability, comprising:

- obtaining the comprehensive evaluation value of the patient's current spontaneous breathing ability, and comparing the comprehensive evaluation value of the patient's current spontaneous breathing ability with a preset offline threshold;
- wherein if the comprehensive evaluation value of the patient's current spontaneous breathing ability is less than the preset offline threshold, it is determined that the patient does not meet the offline requirements, and at the same time, determine that the patient's current comprehensive evaluation value of spontaneous breathing ability is different from the preset offline threshold a threshold difference, and based on the difference, estimate the duration of use of the ventilator device by the patient;
- feeding back the estimated result to the patient's smart terminal;
- otherwise it is determined that the patient meets the off-line requirement, and the off-line operation on the patient is completed.

Preferably, a device for solving the off-line of the patient's ventilator based on the mixed gas comprising:

- a gas mixing module configure to mix carbon dioxide and oxygen based on the initial mixing concentration and deliver the mixed gas to the patient based on the ventilator device;
- a concentration changing module configured to monitor the patient's partial pressure of carbon dioxide in real time based on the delivery result, and to change the initial mixed concentration of carbon dioxide and oxygen in a gradient based on the partial pressure of carbon dioxide; and
- an evaluation module configured to obtain the patient's respiratory muscle function data based on the gradient change result, evaluate the respiratory muscle function data, and complete the patient's ventilator off-line based on the evaluation result.

Additional features and advantages of the invention will be set forth in the description which follows, and in part will be apparent from the description, or may be learned by practice of the invention. The objectives and other advantages of the invention may be realized and attained by the structure particularly pointed out in the written description and claims hereof as well as the appended drawings.

The technical solutions of the present invention will be described in further detail below with reference to the accompanying drawings and embodiments.

BRIEF DESCRIPTION OF THE DRAWINGS

The accompanying drawings are used to provide a further understanding of the present invention, and constitute a part of the description, and are used to explain the present invention together with the embodiments of the present invention, and do not constitute a limitation to the present invention. In the attached picture.

DETAILED DESCRIPTION OF THE PREFERRED EMBODIMENT

The preferred embodiments of the present invention will be described below in conjunction with the accompanying drawings. It should be understood that the preferred embodiments described here are only used to illustrate and explain the present invention, and are not intended to limit the present invention.

Embodiment 1 comprising: s

Figure 1:
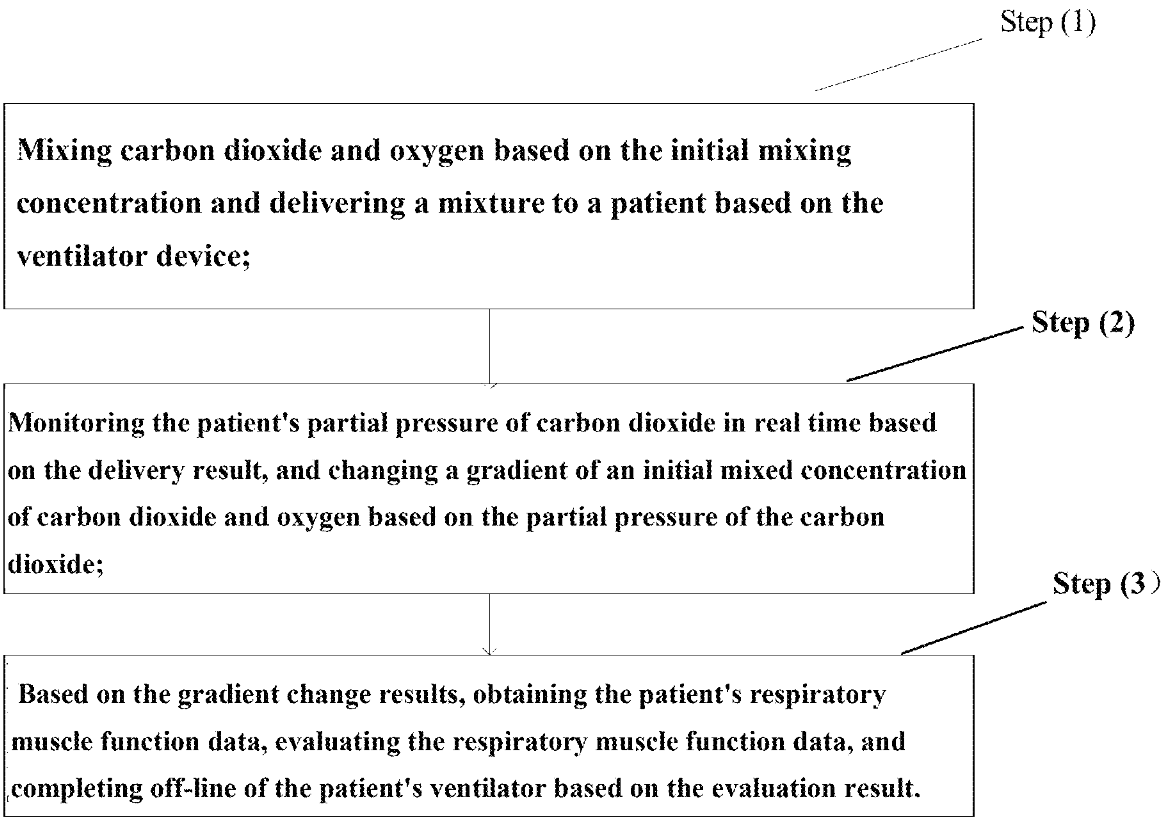
FIG. 1 is a flowchart of a method for solving a patient ventilator off-line based on mixed carbon dioxide gas in an embodiment of the present invention.

As shown in FIG. 1, the embodiment 1 provides a method for solving ventilator off-line problems on patients based on mixed gases, comprising:

- Step (1): mixing carbon dioxide and oxygen based on the initial mixing concentration and delivering the mixture to the patient based on the ventilator device;
- Step (2): monitoring the patient's partial pressure of carbon dioxide in real time based on the delivery result, and changing the initial mixed concentration of carbon dioxide and oxygen in a gradient based on the partial pressure of carbon dioxide; and
- Step (3): obtaining the patient's respiratory muscle function data based on the gradient change result, and evaluating the respiratory muscle function data, and complete the off-line of the patient's ventilator based on the evaluation result.

In this embodiment, the initial mixed concentration refers to the mixing of the minimum control concentration of carbon dioxide and oxygen according to the ventilator device, in order to allow the patient to adapt from the lowest carbon dioxide concentration, thereby get off the ventilator.

In this embodiment, the partial pressure of carbon dioxide refers to the partial pressure of the patient's end-tidal carbon dioxide (EtCO2) and arterial carbon dioxide (PaCO2); wherein the partial pressure of the patient's end-tidal carbon dioxide (EtCO2) is configured to indicate ventilation condition in lungs of the patients, and arterial carbon dioxide (PaCO2) is configured to indicate an amount of carbon dioxide in the patient's arterial blood.

In this embodiment, the gradient change refers to increasing the concentration of carbon dioxide, and the concentration increasing range is 1%-6%.

In this embodiment, the respiratory muscle function data refers to the patient's ability to breathe spontaneously after receiving the mixed gas of carbon dioxide and oxygen at different concentrations, including the breathing rate and so on.

In this embodiment, completing the weaning of the ventilator for the patient based on the evaluation results means that the weaning of the ventilator can be performed when the patient's respiratory muscles can reach a normal standard.

The beneficial effect of the above technical solution is: by mixing a certain concentration of carbon dioxide gas and oxygen, the patient's respiratory nerve center can be stimulated, so as to ensure the stimulation of the patient's active breathing, improve the stability of the treatment, and ensure the recovery of the patient's respiratory function. The effect and efficiency of the machine can reduce the pain of patients when they are offline.

Embodiment 2

Figure 2:
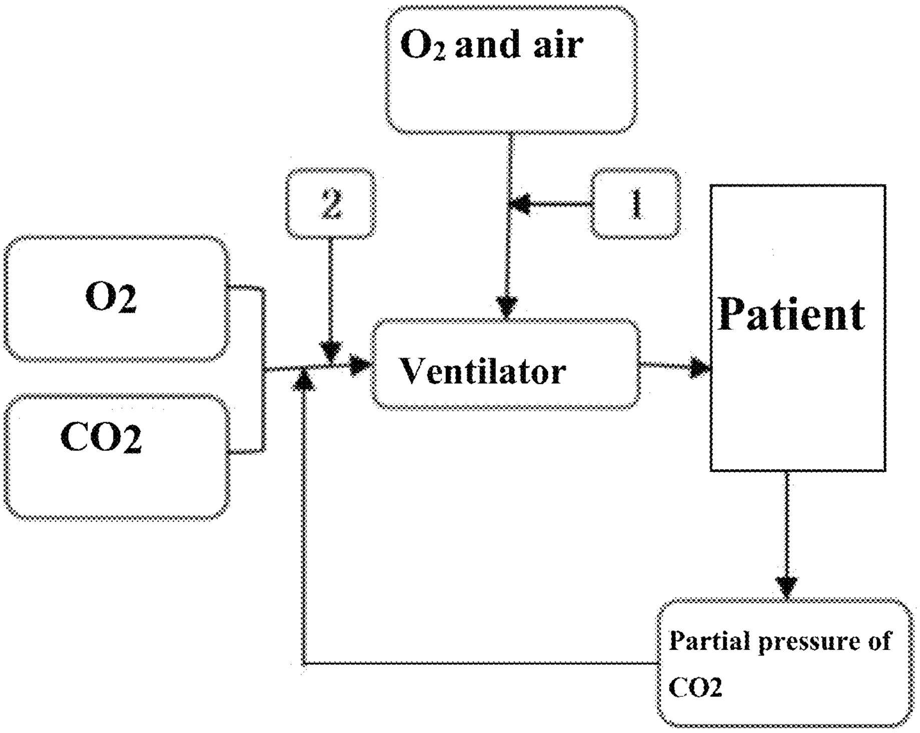
FIG. 2 is a schematic diagram of a method for solving a patient ventilator off-line based on mixed carbon dioxide gas in an embodiment of the present invention.

On the basis of the above-mentioned embodiment 1, this embodiment provides a method for solving the off-line of the patient's ventilator based on mixed gas, as shown in FIG. 2, in step (1), carbon dioxide and oxygen are mixed based on the initial mixed concentration, comprising:

- obtaining the current working parameters of the ventilator device, and determining the target oxygen supply mode of the ventilator device based on the current working parameters, wherein the target oxygen supply mode is a standard oxygen supply mode or an offline oxygen supply mode;
- when the target oxygen supply mode is a standard oxygen supply mode, switch the target oxygen supply mode of the ventilator device based on a preset switching valve;
- when the target oxygen supply mode is an offline oxygen supply mode, obtain the control range of the breathing apparatus for the carbon dioxide concentration, and determine the initial mixed concentration of carbon dioxide based on the control range; and
- based on the initial mixing concentration, respectively inputting the carbon dioxide and oxygen into the target container through the airway tube for mixing to obtain a mixed gas of carbon dioxide and oxygen.

In this embodiment, the current working parameter may be the type of the current gas supply source of the ventilator device and the concentration or ratio of the gas supply to different gas supply sources.

In this embodiment, the target oxygen supply mode comprise two modes, namely a standard oxygen supply mode and an offline oxygen supply mode, wherein the standard oxygen supply mode is to mix oxygen with air, and the offline oxygen supply mode is to mix oxygen with carbon dioxide.

In this embodiment, the preset switching valve is set in advance in the ventilator device and is used to switch the oxygen supply mode.

In this embodiment, the control range is 1%-6%.

In this embodiment, the target container is pre-set in the ventilator device to fully mix the oxygen and carbon dioxide.

The beneficial effect of the above technical solution is: by determining the oxygen supply mode of the ventilator device, and when the oxygen supply mode of the ventilator device is the standard oxygen supply mode, the oxygen supply mode of the ventilator device is switched when it needs to be switched, and at the same time When switching to the offline oxygen supply mode, the carbon dioxide and oxygen are mixed, which facilitates stable treatment of the patient and ensures the recovery of the patient's respiratory function.

Embodiment 3

On the basis of the above-mentioned embodiment 2, this embodiment provides a method based on the mixed gas to solve the off-line of the patient's ventilator. Based on the initial mixed concentration, respectively mixing the carbon dioxide and oxygen into the target container through the airway tube, comprises:

- sampling the carbon dioxide based on a preset sampling device, and detecting the concentration of the sampled carbon dioxide to obtain the detection concentration of the carbon dioxide;
- comparing the detected concentration with the initial mixed concentration;
- if there is a difference between the detected concentration and the initial mixed concentration, it is determined that there is a defect in the mixing of carbon dioxide and oxygen, and an alarm operation is performed, and the operation of inputting the mixed gas to the patient is terminated simultaneously;
- otherwise, it is determined that the mixing of carbon dioxide and oxygen is qualified, and the process of mixing carbon dioxide and oxygen is detected in real time until the patient is off the ventilator.

In this embodiment, the preset sampling device is set in advance and is used for random sampling of carbon dioxide, the purpose of which is to detect whether the concentration of carbon dioxide is consistent with the initial mixed concentration.

The beneficial effects of the above technical solution are as follows. During the mixing process of carbon dioxide and oxygen, random collection of carbon dioxide and detection of the current concentration ensures strict control of the concentration of carbon dioxide, and improves the offline security of ventilators for patients by mixing carbon dioxide gas.

Embodiment 4

On the basis of the above-mentioned embodiment 1, this embodiment provides a method based on the mixed gas to solve the patient's ventilator offline. In step (1), the mixed gas is delivered to the patient based on the ventilator device, comprising:

- acquiring the patient's sign parameters, and determine the oxygen supply pressure and oxygen supply rate to the patient based on the sign parameters;
- adjusting the operating parameters of the ventilator device based on the oxygen supply pressure and oxygen supply rate, and detecting the airtightness of the inspiratory tube of the ventilator device based on the adjustment result;

wherein if the airtightness is intact, the mixed gas of carbon dioxide and oxygen is delivered to the patient;

otherwise, the inspiratory tube is replaced, and the mixed gas is delivered to the patient based on the result of the replacement.

In this embodiment, the sign parameters refer to the patient's pulse, heart rate, and blood pressure.

In this embodiment, the operating parameters refer to parameters such as working power and working current of the ventilator device. In this embodiment, the airtightness is used to characterize whether the suction pipe leaks.

The beneficial effect of the above technical solution is: by analyzing the patient's sign parameters, the oxygen supply pressure and the oxygen supply rate of the ventilator device can be adjusted according to the patient's signs, so as to ensure the stable and effective delivery of the mixed gas to the patient. The treatment effect of the patient is guaranteed, and at the same time, it is convenient for the patient to quickly recover the spontaneous breathing function, and the efficiency of the off-line ventilator is improved.

Embodiment 5

On the basis of the above-mentioned embodiment 4, this embodiment provides a method for solving the off-line of the patient's ventilator based on the mixed gas, and the mixed gas of carbon dioxide and oxygen is delivered to the patient based on the inspiratory tube, comprising:

obtaining the time information of the patient receiving the mixed gas of carbon dioxide and oxygen and the gas volume of the mixed gas, and obtain the identity information of the patient;

constructing the patient treatment electronic data sheet based on the time information, gas volume and identity information, and typesetting the patient treatment electronic data table to obtain the target recording areas of the time information, gas volume and identity information respectively; and recording time information, gas volume and identity information based on the target recording area, and updating the gas volume of the mixed gas received by the patient in the patient treatment electronic data sheet in real time.

In this embodiment, the identity information comprises the patient's name, age and ID number.

In this embodiment, the patient treatment electronic data sheet is used to record various parameters of the patient when receiving the mixed gas treatment and the patient's identity information, so as to facilitate an intuitive understanding of the patient's acceptance of the mixed carbon dioxide gas.

In this embodiment, typesetting refers to setting the table style and data record format in the patient treatment electronic data sheet accordingly.

In this embodiment, the target recording area refers to the cells of the patient treatment electronic data sheet for recording time information, gas volume and identity information respectively.

The beneficial effect of the above technical solution is: by recording the time, gas volume and identity information of the patient receiving the mixed gas, it is convenient to check the current situation of the patient receiving the mixed gas intuitively, and at the same time, it is convenient to timely accept the patient according to the electronic data sheet. The concentration of the mixed gas is adjusted to improve the rigor and safety for patients to solve the off-line of the ventilator by mixing carbon dioxide gas.

Embodiment 6

On the basis of the above-mentioned embodiment 1, this embodiment provides a method based on mixed gas to solve the off-line of the patient's ventilator. In step (2), monitoring the partial pressure of carbon dioxide of the patient in real time based on the delivery result, and based on the partial pressure of carbon dioxide Gradient changes in the initial mixed concentration of carbon dioxide and oxygen, comprising:

based on the ventilator device, continuously inputting the mixed gas of the initial mixed concentration to the patient for a preset period of time, and the partial pressure of carbon dioxide of the patient is monitored in real time, wherein the partial pressure of carbon dioxide comprises arterial partial pressure of carbon dioxide and end-tidal partial pressure of carbon dioxide;

determining the target value of the partial pressure of carbon dioxide of the patient at different time points based on the monitoring results, and obtaining a numerical sequence of the partial pressure of carbon dioxide of the patient within a preset time period;

matching the target chart from the preset chart template library based on the numerical sequence, and determining the horizontal and vertical coordinate legends of the two-dimensional coordinates of the target chart based on the attribute information of the preset time period and the target value of the numerical sequence, wherein the legend on the abscissa is time, and the legend on the ordinate is the target value of the numerical sequence;

determining the configuration parameters of the target chart, and performing format conversion on the numerical sequence of the partial pressure of carbon dioxide based on the configuration parameters to obtain the partial pressure of carbon dioxide visual graph; and determining the maximum value and the minimum value of the partial pressure of carbon dioxide of the patient in the preset time period based on the partial pressure of carbon dioxide visual map, and determine the maximum value and the minimum value based on the maximum value and the minimum value.

The fluctuation range of the patient's partial pressure of carbon dioxide;

Comparing the stated fluctuation range with the standard allowable range;

If the fluctuation range is not within the allowable range of the standard, it is determined that the patient's inhalation of the mixed gas is abnormal;

Otherwise, it is determined that there is no abnormality in the patient's inhalation of the mixed gas, and at the same time, the pH value in the patient's body is obtained;

Determine the difference between the pH value and the standard pH value, and when the difference is within the preset allowable fluctuation range, it is determined that the patient has adapted to the mixed gas of the initial mixed concentration, and the ventilator Device feedback judgment result;

Based on the received feedback determination result, control the ventilator device to change the initial mixed concentration of carbon dioxide and oxygen by gradient, and continuously monitor the partial pressure of carbon dioxide of the patient until the initial mixed concentration reaches a maximum allowed value of the gradient change, wherein the allowed range of the gradient change is 1%-6%.

In this embodiment, the principle of monitoring the partial pressure of carbon dioxide of the patient in real time and gradiently changing the initial mixed concentration of carbon dioxide and oxygen based on the partial pressure of carbon dioxide is: carbon dioxide maintains pH balance through the reaction of $CO2+H2O \rightarrow H+HCO3$, so changes in carbon dioxide will cause changes in pH, all cell functions in the brain and body are generally affected by pH, human life only allows small changes in pH, because the CO2 and H ions produced by metabolism is in a state of rapid equilibrium (CO2/H+ state) and can be cleared by pulmonary ventilation, the dynamic control of respiration by CO2 provides the main homeostatic mechanism for acute regulation of acid-base state.

The mechanism of CO2/H+ homeostasis has implications for the regulation and control of respiration. Low-level hypercapnia can cause irritation of the respiratory system and increased respiratory rate, mainly due to the direct effect of increased CO2/H+ on the carotid body and very few brainstem structures, comprising the posterior trapezium of chemoreceptors Nuclei (RTN) and a subset of serotonergic neurons play a large role.

The CO2/H+ homeostasis mechanism is regulated by the $CO2+H2O \rightarrow H+HCO3$—reaction by inhaling and exhaling CO2. High gain of hypercapnic carbon dioxide (CO2) ventilation chemoreflex caused induces respiratory stimulation, with elevated PaCO2.

The CO2/H+ homeostasis mechanism proceeds through a complex mechanism. At rest, respiratory chemoreflexes initiated at peripheral and central sites mediate rapid stabilization of arterial PaCO2 and pH. Specific brainstem neurons (eg, posterior trapezoidal nucleus, RTN; serotonergic) are activated by PaCO2 and stimulate respiration. RTN neurons detect CO2 through endogenous proton receptors (TASK-2, GPR4), synaptic inputs from peripheral chemoreceptors, and signals from astrocytes. Respiratory chemoreflexes depend on arousal, and stimulation of chemoreceptors leads to arousal. When the two are abnormal, these interactions can lead to sleep-disordered breathing. During exercise, despite increased metabolic activity, central commands and reflexes from the exercising muscles produce the required respiratory stimulation to maintain arterial PaCO2 and pH.

In this embodiment, the purpose of changing the mixed gas concentration gradient is: After the patient inhales the breathing gas containing a certain proportion of carbon dioxide gas, it is absorbed by the human body, so that the pH in the patient's body decreases and the arterial CO2 partial pressure increases. Central chemoreceptor serotonergic neurons (serotonergicneurons) located in the ventral medulla and posterior trapezoidal nucleus sense the decrease in central nervous system pH caused by elevated arterial carbon dioxide. The respiratory centers within the medulla and pons then generate a unified neural signal that is sent to the main muscles of respiration, producing respiration. In this way, the active breathing can be stimulated by inhaling a certain amount of CO2, and the patient's spontaneous breathing function can be quickly and effectively restored.

In this embodiment, the preset time period is set in advance, such as one day, two days, etc., and can be adjusted according to medical conditions.

In this embodiment, the end-tidal partial pressure of carbon dioxide is used to reflect pulmonary ventilation and pulmonary blood flow.

In this embodiment, the target value refers to the specific number of partial pressure of carbon dioxide of the patient at different time points. The value is convenient for an effective understanding of the patient's breathing condition.

In this embodiment, the numerical sequence refers to the sequence obtained by sequentially arranging the target values of the partial pressure of carbon dioxide according to time sequence.

In this embodiment, the preset chart template library is set in advance, and different types of chart templates are stored inside.

In this embodiment, the target chart refers to a chart suitable for displaying the patient's partial pressure of carbon dioxide.

In this embodiment, the attribute information refers to a data type of a preset time period, that is, "time".

In this embodiment, the configuration parameters refer to the composition of the target image and the format requirements of the data to be displayed.

In this embodiment, the visible graph of the partial pressure of carbon dioxide refers to the chart information obtained by displaying the partial pressure of carbon dioxide using a target image.

In this embodiment, the standard allowable range is set in advance and is used to measure whether the patient is breathing normally.

In this embodiment, the preset allowable fluctuation range is set in advance and is used to measure the pH in the patient's body. In the case of changing values, the range is generally small.

In this embodiment, gradient change refers to sequentially increasing the concentration of carbon dioxide from 1% to 6%.

The beneficial effect of the above-mentioned technical solution is: by continuing to perform image visualization on the patient's partial pressure of carbon dioxide It is easy to accurately analyze the fluctuation range of the patient's partial pressure of carbon dioxide, so as to ensure that the patient's partial pressure of carbon dioxide remains within the normal range. Secondly, judge the pH value in the patient's body, and when the pH change is within the set range At the same time, the gradient change of the patient's carbon dioxide is completed, which ensures the safety of the patient when the carbon dioxide concentration is changed, and at the same time facilitates the patient to quickly and effectively achieve off-line, reducing the pain during off-line.

Embodiment 7

On the basis of the above-mentioned embodiment 6, this embodiment provides a method for solving the patient's ventilator offline based on the mixed gas, and it is determined that the patient's inhalation of the mixed gas is abnormal, comprising:

obtaining the comparison result between the fluctuation range and the standard allowable range, and when it is determined that the patient's inhalation of the mixed gas is abnormal, generate a target control instruction;

based on the target control instruction, controlling the ventilator device to stop delivering the mixed gas to the patient, and collecting a preset amount of the mixed gas, and at the same time acquiring the current sign data of the patient, wherein an amount of the sign data is at least one;

detecting the mixed gas, respectively determining the ratio of carbon dioxide and oxygen in the mixed gas example, and verifying the ratio based on the preset ratio;

wherein if it fails to pass the verification, it is determined that the ventilator device has a defect in the mixing process of the carbon dioxide and oxygen, and a first alarm is carried out; and if the verification is passed, then the current sign data of the patient is analyzed to determine whether there is any abnormality in the current characteristic data of the patient, and if there is any abnormality, the second alarm is carried out;

respectively recording the first alarm and the second alarm to obtain the abnormal situation report sheet of the patient in the off-line process of the ventilator.

In this embodiment, the target control instruction is generated by the ventilator device itself, and is used to control the corresponding device to stop delivering the mixed gas to the patient.

In this embodiment, the preset amount is set in advance and is used for analyzing the ratio of carbon dioxide and oxygen in the mixed gas.

In this embodiment, the sign data refers to the patient's current respiratory rate, pulse, blood pressure, and the like.

In this embodiment, the preset ratio is set in advance and is used to characterize the standard ratio of carbon dioxide and oxygen in the mixed gas.

In this embodiment, the first alarm refers to the alarm performed when there is an abnormality in the mixed gas, which may be an audible alarm.

In this embodiment, the second alarm refers to an alarm performed when there is an abnormality in the patient's sign data, which may be a light alarm.

In this embodiment, the abnormal situation report sheet refers to recording the abnormal situation existing in the process of resolving the ventilator offline, so that patients and doctors can check the abnormal cause in time.

The beneficial effect of the above technical solution is: through the analysis of the ratio of carbon dioxide and oxygen in the mixed gas and the patient's sign data respectively, it is ensured that the cause of the abnormal partial pressure of carbon dioxide is found, thereby ensuring that the patient is in the process of solving the off-line of the ventilator and providing a reliable safety guarantee for patients.

Embodiment 8

On the basis of the above-mentioned embodiment 1, this embodiment provides device for solving ventilator off-line problems on patients based on mixed gases in step (3), obtaining the patient's respiratory muscle function data based on the gradient change result, evaluating the respiratory muscle function data, and weaning the patient's ventilator off based on the evaluation result, comprising:

obtaining the respiratory waveform data of the patient after gradiently changing the initial mixed concentration of the mixed gas based on the preset sensor, and fitting the respiratory waveform data to obtain the respiratory wave curve of the patient;

obtaining a reference respiratory wave curve, and superimposing the reference respiratory wave curve with the patient's respiratory wave curve, wherein the reference respiratory wave curve is obtained from training based on historical training data;

determining a difference area between the respiratory wave curve and the reference respiratory wave curve based on the superposition result, and extracting the waveform features of the respiratory wave curve in the difference area;

determining the curve parameters of the patient's respiratory wave curve in the difference area based on the waveform characteristics, and process the curve parameters to obtain the patient's breathing data in the difference area;

extracting the attribute information of the respiratory data, and match the target data cleaning rules from the preset data cleaning rule base based on the attribute information;

cleaning the breathing data based on the target data cleaning rules to obtain the respiratory muscle function data of the patient;

constructing a spontaneous breathing capacity assessment model, and inputting the respiratory muscle function data into the spontaneous breathing capacity assessment model for processing, determining the current respiratory rate of the patient, and simultaneously determining the respiratory intensity of the patient based on the current respiratory rate;

respectively determining the weight of the respiratory rate and respiratory intensity in the evaluation process of spontaneous breathing ability value, and obtaining the comprehensive evaluation value of the patient's current spontaneous breathing ability based on the weight value; and displaying comprehensive evaluation value of the patient's current spontaneous breathing ability on the ventilator device, and at the same time, transmitting the comprehensive evaluation value of the patient's current spontaneous breathing ability to the doctor's smart terminal to complete the evaluation of the patient's spontaneous breathing ability.

In this embodiment, the preset sensor is set in advance and is used to detect the breathing condition of the patient.

In this embodiment, the reference respiratory wave curve refers to the patient's respiratory wave curve should be, the presented state is obtained by analyzing and training multiple groups of patients' breathing data, and is an average value.

In this embodiment, the difference area refers to the area where there are different curve segments between the patient's respiratory wave curve and the reference respiratory wave curve.

In this embodiment, the waveform feature refers to the curve shape, fluctuation amplitude, etc. of the respiratory wave curve.

In this embodiment, the curve parameter refers to the specific value of the respiratory wave curve in the difference area, comprising the amplitude and period of the respiratory wave curve in this area.

In this embodiment, the attribute information refers to the data type in the respiratory data.

In this embodiment, the preset data cleaning rule library is set in advance, and cleaning rules corresponding to different types of data are stored inside.

In this embodiment, the target data cleaning rule refers to a data cleaning rule suitable for cleaning respiratory data, which is one or more combinations in the preset data cleaning rule library.

In this embodiment, the comprehensive evaluation value of the patient's current spontaneous breathing ability is a parameter used to characterize the strength of the patient's spontaneous breathing ability.

In this embodiment, obtaining the comprehensive evaluation of the patient's current spontaneous breathing ability based on the weight values, comprising:

obtaining the current respiratory rate of the patient, and calculate the respiratory effort index of the patient based on the respiratory rate, and calculating the comprehensive evaluation value of the patient's current spontaneous breathing capacity based on the respiratory effort index, and the specific steps comprise:

obtaining the lung compliance value and respiratory rate of the patient, and performing dimensionless processing on the lung compliance value and respiratory rate to obtain lung compliance value parameters and respiratory rate parameters;

calculating the respiratory effort index of the patient according to the following formula:

$$\alpha = \frac{e^{\mu} * \beta * \frac{p}{P} * \frac{\tau}{\vartheta}}{f};$$

wherein, α represents the respiratory effort index of the patient, and the value range is (1, 30); μ represents the error factor, and the value range is (0.02, 0.05); β represents the lung compliance value parameter of the patient; p represents the maximum inspiratory pressure of the patient; P represents the airway closure pressure of the patient; τ represents arterial partial pressure of oxygen of the patient; ϑ represents the partial pressure of alveolar oxygen of the patient; f represents the respiratory rate parameter of the patient;

calculating the comprehensive evaluation value of the patient's current spontaneous breathing capacity according to the following formula:

$$Q = \frac{\rho * f(f) + \omega * f(\lambda) + \eta * f(\alpha)}{3};$$

wherein Q represents the comprehensive evaluation value of the patient's current spontaneous breathing ability; ρ represents the weight value of the patient's respiratory rate; ω represents the weight value of the patient's respiratory intensity; η represents the weight value of the patient's respiratory effort index; f(f) presents the patient's respiratory rate evaluation function; f(λ) represents the patient's respiratory intensity evaluation function; f(α) represents the patient's respiratory effort index evaluation function; and λ represents the patient's respiratory intensity value;

comparing the comprehensive evaluation value with the preset evaluation value;

wherein if the comprehensive evaluation value is greater than or equal to the preset evaluation value, it is determined that the patient meets the offline condition, processing offline on the patient;

otherwise, it is determined that the patient does not meet offline conditions.

The respiratory effort index is a parameter used to reflect the ventilation and oxygen exchange functions of the patient's lungs. The above parameter of lung compliance value refers to the amount of change in lung volume caused by a change in unit pressure.

The comprehensive evaluation value of the patient's current spontaneous breathing ability is a parameter used to characterize the strength of the patient's spontaneous breathing ability. The larger the value, the stronger the patient's spontaneous breathing ability.

The above preset evaluation values are set in advance.

The beneficial effect of the above technical solution is: by monitoring the patient's respiratory wave curve, accurate and effective analysis of the patient's breathing conditions under different concentrations of carbon dioxide is realized, and at the same time, the user can accurately obtain the patient's breathing conditions under different concentrations of carbon dioxide gas and at different time points. Respiratory muscle skill data, to achieve accurate and effective evaluation of the patient's spontaneous breathing ability under different concentrations of carbon dioxide, so as to facilitate timely and effective offline operation of the patient's ventilator according to the evaluation results, improving the safety and effectiveness of offline Sex, but also to ensure the efficiency and effectiveness of offline.

Embodiment 9

On the basis of the above-mentioned embodiment 8, this embodiment provides a solution based on mixed gas, a method for taking the machine off-line is to obtain the comprehensive evaluation value of the patient's current spontaneous breathing ability based on the weight value, comprising:

obtaining the comprehensive evaluation value of the patient's current spontaneous breathing ability, and comparing the comprehensive evaluation value of the patient's current spontaneous breathing ability with a preset offline threshold;

wherein if the comprehensive evaluation value of the patient's current spontaneous breathing ability is less than the preset offline threshold, it is determined that the patient does not meet the offline requirements, and at the same time, determine that the patient's current comprehensive evaluation value of spontaneous breathing ability is different from the preset offline threshold a threshold difference, and based on the difference, estimate the duration of use of the ventilator device by the patient;

feeding back the estimated result to the patient's smart terminal;

otherwise, it is determined that the patient meets the off-line requirement, and the off-line operation on the patient is completed.

In this embodiment, the preset threshold is set in advance and is used to measure whether the patient meets the weaning condition.

The beneficial effect of the above technical solution is: by providing a reference basis for whether offline operation can be performed according to the evaluation results, it is convenient to ensure that the offline operation is performed under the premise of patient safety, and the safety and efficiency of solving the patient's ventilator offline are improved.

Embodiment 10

Figure 3:
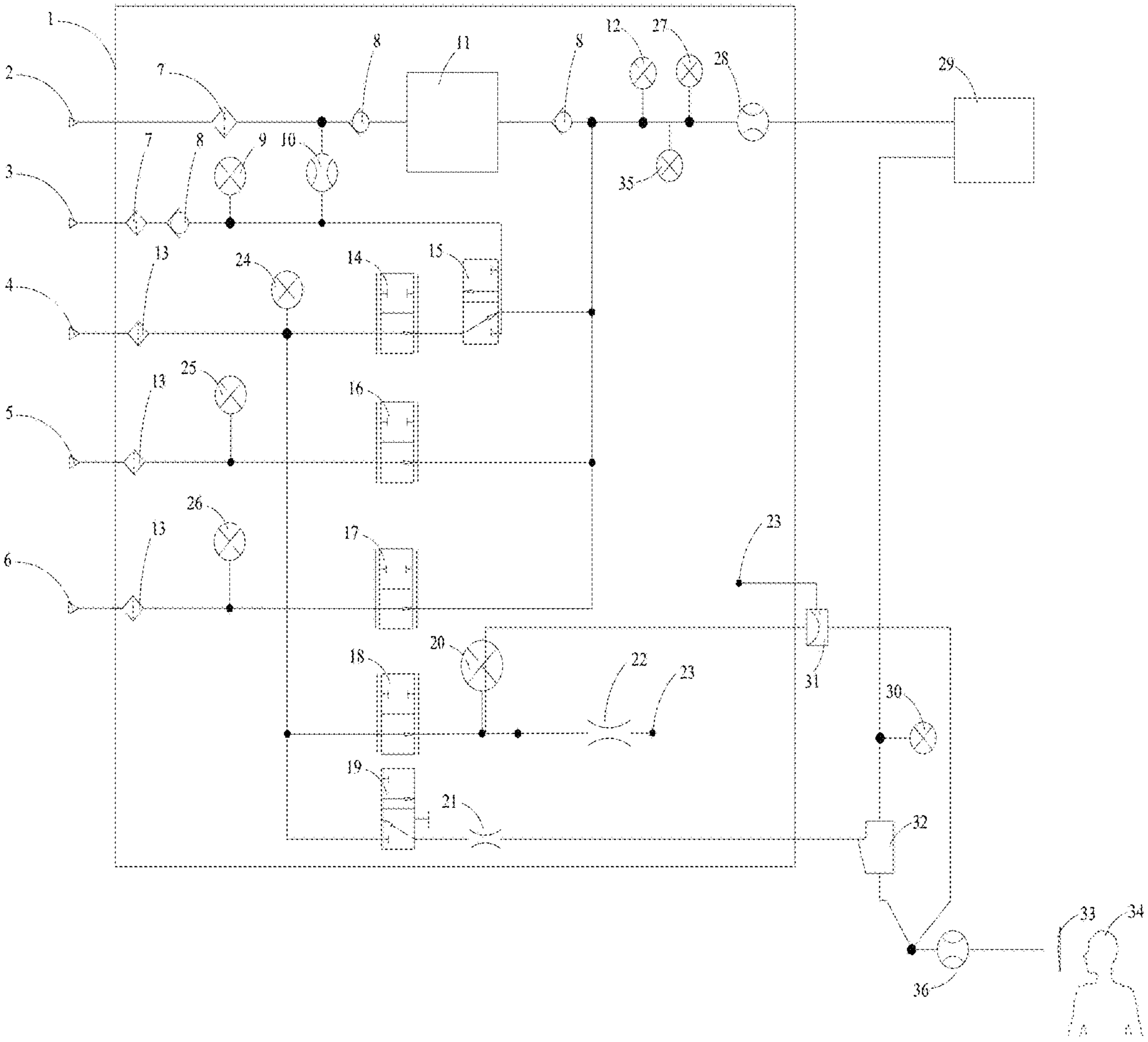
FIG. 3 is a structural diagram of a device for solving a patient's ventilator off-line based on mixed carbon dioxide gas in an embodiment of the present invention-.
Figure 4:
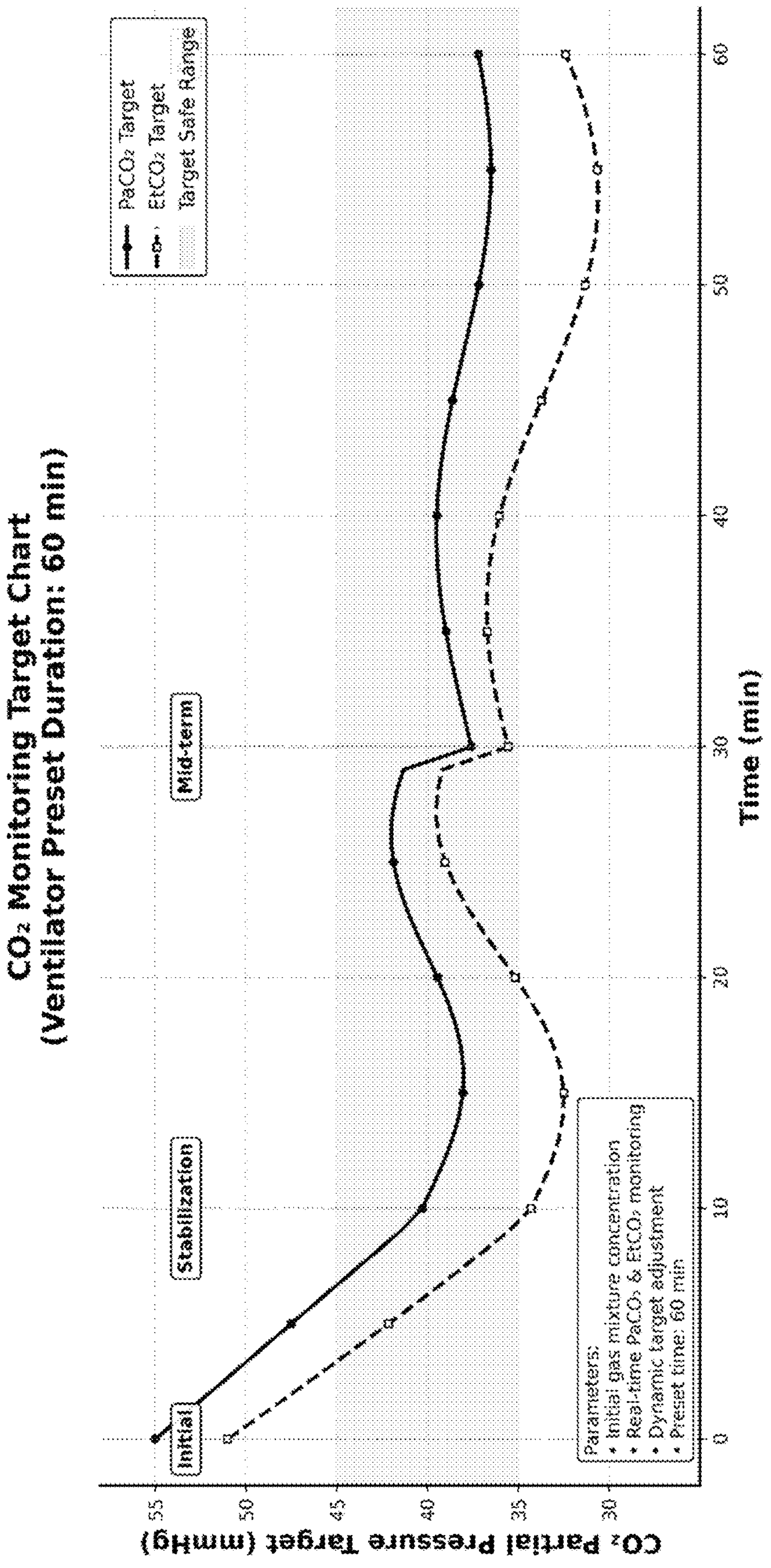
FIG. 4 is a target chart according to an embodiment 7 of the present invention.
Figure 5:
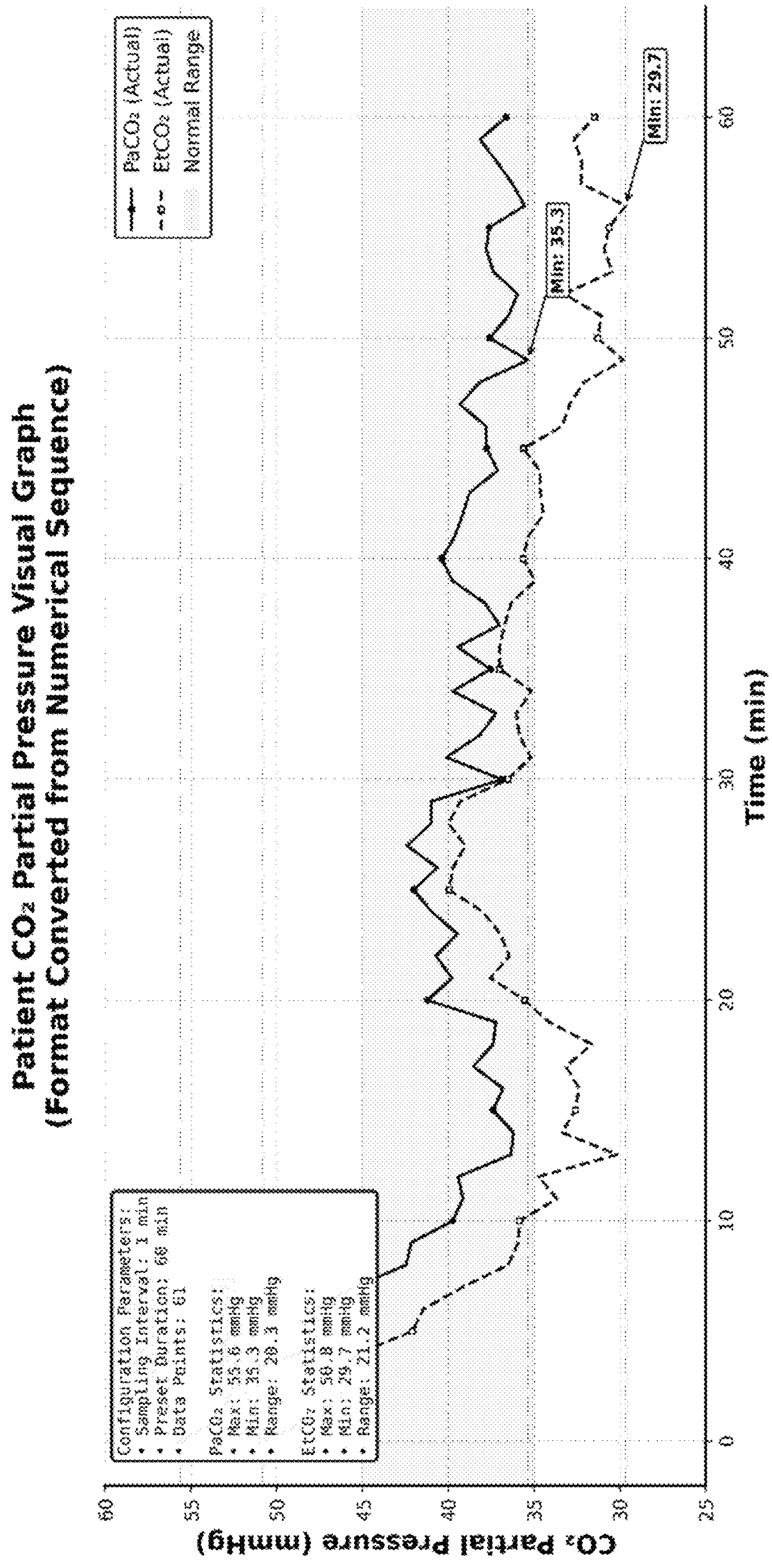
FIG. 5 is a visual graph of the patient's partial pressure of carbon dioxide according to the embodiment 7 of the present invention.

As shown in FIG. 3, the embodiment provides a device for solving ventilator off-line problems on patients based on mixed gases, comprising:

a gas mixing module configured to mix carbon dioxide and oxygen based on the initial mixing concentration and delivering the mixed gas to the patient based on the ventilator device;

a concentration changing module, configured to monitor the patient's partial pressure of carbon dioxide in real time based on the delivery result, and to change the initial mixed concentration of carbon dioxide and oxygen in a gradient based on the partial pressure of carbon dioxide; and an evaluation module configured to obtain the patient's respiratory muscle function data based on the gradient change result, evaluate the respiratory muscle function data, and complete the patient's ventilator off-line based on the evaluation result.

In this embodiment, a device structure diagram for solving the off-line of a patient ventilator based on mixed gas is shown in FIG. 3: among them, the ventilator system device body 1, air source inlet 2, low-pressure oxygen source 3, high-pressure oxygen gas source 4, first treatment gas port 5, second treatment gas port 6, first filter 7, check valve 8, first pressure sensor 9, first flow sensor 10, blower 11, second pressure sensor 12, The second filter 13, the first flow control valve 14, the direction control valve 15, the second flow control valve 16, the third flow control valve 17, the fourth flow control valve 18, the on-off valve 19, the third pressure sensor 20, First throttle valve 21, second throttle valve 22, pipe outlet 23, second pressure sensor 24, second pressure sensor 25, second pressure sensor 26, oxygen sensor 27, second flow sensor 28, heating humidifier 29, respiratory pressure sensor 30, exhaust valve 31, drug nebulizer 32, breathing catheter 33, inspiratory pipeline 34, oxygen (or carbon dioxide) concentration sensor 35

The beneficial effect of the above technical solution is: by mixing a certain concentration of carbon dioxide gas and oxygen, the patient's respiratory nerve center can be stimulated, so as to ensure the stimulation of the patient's active breathing, improve the stability of the treatment, and ensure the recovery of the patient's respiratory function. The effect and efficiency of the machine can reduce the pain of patients when they are offline.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A device for solving ventilator weaning problems of a patient based on mixed gases, comprising:

a controller comprising:

a gas mixing module configured to mix carbon dioxide and oxygen to an initial mixture concentration and deliver the initial mixture concentration to the patient via a ventilator device;

a concentration changing module, configured to monitor the patient's partial pressure of carbon dioxide in real time after delivery of the initial mixture concentration, and change the initial mixture concentration of carbon dioxide and oxygen based on the patient's partial pressure of carbon dioxide; and an evaluation module configured to obtain the patient's respiratory muscle function data and evaluate the respiratory muscle function data based on the change in mixture concentration, and configured to wean the patient from ventilation based on an evaluation result;

wherein the concentration changing module is configured to:

based on the ventilator device, continuously input the initial mixture concentration to the patient for a preset time period, and monitor the patient's partial pressure of carbon dioxide of the patient in real time, wherein the patient's partial pressure of carbon dioxide comprises an arterial partial pressure of carbon dioxide and end-tidal partial pressure of carbon dioxide;

determine a target value of the patient's partial pressure of carbon dioxide at different time points based on a monitoring results, and obtain a numerical sequence of the target value of the patient's partial pressure of carbon dioxide within the preset time period, and form a target chart; and match the target chart from a preset chart template library based on the numerical sequence, and determine a horizontal and a vertical coordinate legends of two-dimensional coordinates of the target chart based on attribute information of the preset time period and the target value of the numerical sequence, wherein the horizontal coordinate legend is time, and the vertical coordinate legend is the target value of the numerical sequence;

determine configuration parameters of the target chart, and perform format conversion on the numerical sequence based on the configuration parameters to obtain a visual graph of the patient's partial pressure of carbon dioxide;

determine a maximum value and a minimum value of the patient's partial pressure of carbon dioxide in the preset time period based on the visual graph, and determine the patient's carbon dioxide concentration based on the maximum value and the minimum value of the patient's carbon dioxide pressure within a fluctuation range;

compare the stated fluctuation range with a standard allowable range;

wherein if the fluctuation range is not within the standard allowable range, determine that an inhalation of the initial mixture concentration by the patient is abnormal; and otherwise, determine that there is no abnormality in the patient's inhalation, and simultaneously, obtain a pH value in the patient's body;

determine a difference between the pH value and a standard pH value, and when the difference is within a preset allowable fluctuation range, determine that the patient has adapted to the initial mixture concentration, and determine a ventilator device feedback judgment result based on whether the patient's inhalation is abnormal and/or the patient has adapted; and based on the feedback determination result, gas mixing module is configured to control the ventilator device to change the initial mixture concentration of carbon dioxide and oxygen within a gradient, and the concentration changing module is configured to continuously monitor the patient's partial pressure of carbon dioxide until the changed mixture concentration reaches a maximum allowed value, wherein an allowed range of the gradient is 1%-6%;

wherein the evaluation module is configured to:

obtain patient's respiratory waveform data after changing the initial mixture concentration via a preset sensor, and fitting the patient's respiratory waveform data to obtain a patient's respiratory wave curve;

obtain a reference respiratory wave curve, and superimpose the reference respiratory wave curve with the patient's respiratory wave curve, wherein the reference respiratory wave curve is obtained from training based on historical training data;

determine a difference domain between the patient's respiratory wave curve and the reference respiratory wave curve after superimposing, and extract waveform features of the patient's respiratory wave curve in the difference domain;

determine curve parameters of the patient's respiratory wave curve in the difference domain based on the waveform features, and treating the curve parameters to obtain patient's respiratory data in the difference domain;

extract attribute information of the patient's respiratory data, so as to match target data cleaning rules from a preset data cleaning rule base;

clean the patient's respiratory data based on the target data cleaning rules to obtain the patient's respiratory muscle function data;

construct a spontaneous respiratory capacity assessment model, and input the respiratory muscle function data into the spontaneous respiratory capacity assessment model for processing, determine a patient's current respiratory rate, and simultaneously determine a patient's respiratory intensity based on the patient's current respiratory rate;

respectively determine a patient's respiratory rate weight and a patient's respiratory intensity weight during spontaneous respiratory capacity assessment, and obtain a comprehensive evaluation value of patient's current spontaneous respiratory capacity based on the patient's respiratory rate weight and the patient's respiratory intensity weight; and display the comprehensive evaluation value of the patient's current spontaneous respiratory capacity on the ventilator device.

* * * * *